(12) United States Patent
Von Falkenhausen

(10) Patent No.: US 6,635,276 B1
(45) Date of Patent: Oct. 21, 2003

(54) ORAL OR MUCOSAL PREPARATION CONTAINING AN ACTIVE INGREDIENT, WITH CONTROLLED ACTIVE INGREDIENT RELEASE, AND ITS USE

(75) Inventor: Christian Von Falkenhausen, Bonn (DE)

(73) Assignee: KTS Kignabb Therapie-Systeme AG, Andernach (DE)

( * ) Notice: Subject to any disclaimer, the term of this patent is extended or adjusted under 35 U.S.C. 154(b) by 0 days.

(21) Appl. No.: 09/674,904

(22) PCT Filed: May 6, 1999

(86) PCT No.: PCT/EP99/03110
§ 371 (c)(1),
(2), (4) Date: Jan. 4, 2001

(87) PCT Pub. No.: WO99/58107
PCT Pub. Date: Nov. 18, 1999

(30) Foreign Application Priority Data

May 8, 1998 (DE) .......................................... 198 20 529

(51) Int. Cl.⁷ .............................. A61K 9/54; A61K 9/26
(52) U.S. Cl. ...................... 424/458; 424/469; 424/490
(58) Field of Search ................................ 424/489, 469, 424/470, 468, 458, 490, 493, 497, 492, 496, 498

(56) References Cited

U.S. PATENT DOCUMENTS

| | | |
|---|---|---|
| 2,738,303 A | 3/1956 | Blythe |
| 2,996,431 A | 8/1961 | Barry |
| 4,361,546 A | 11/1982 | Stricker et al. |
| 4,459,279 A | 7/1984 | Stricker et al. |
| 4,606,909 A | 8/1986 | Bechgaard et al. |
| 4,882,150 A | * 11/1989 | Kaufman ..................... 424/428 |
| 5,656,291 A | 8/1997 | Olsson et al. |
| 5,716,648 A | 2/1998 | Halskov et al. |

FOREIGN PATENT DOCUMENTS

| | | |
|---|---|---|
| CA | 1326632 | 2/1994 |
| DE | 28 36 447 A1 | 2/1980 |
| DE | 39 18 801 A 1 | 5/1991 |
| DE | 197 11 393 C 1 | 8/1998 |
| EP | 0 080 330 | 6/1983 |
| EP | 0 305 918 A1 | 3/1989 |
| EP | 0 343 993 A1 | 11/1989 |
| EP | 0 636 365 A | 2/1995 |
| WO | WO 85/03437 | 8/1985 |
| WO | 89 03437 | 4/1989 |
| WO | 90 11 070 | 10/1990 |
| WO | 94 28911 | 12/1994 |
| WO | 95 01 787 | 1/1995 |

* cited by examiner

*Primary Examiner*—James M. Spear
(74) *Attorney, Agent, or Firm*—D. Peter Hochberg; Katherine R. Vieyra; Sean Mellino

(57) ABSTRACT

The invention relates to the use of a preparation containing a first group of particles and at least one other group of particles which is not identical to the first group of particles for achieving controlled release of an active ingredient present in the cores of the particles, in particular in the human and veterinary medical sectors. The preparation is administered orally, rectally, vaginally etc. The release of the active ingredient then takes place in the appropriate medium, and there is transmucosal absorption of the active ingredient.

17 Claims, 3 Drawing Sheets

ORAL OR MUCOSAL PREPARATION CONTAINING AN ACTIVE INGREDIENT, WITH CONTROLLED ACTIVE INGREDIENT RELEASE, AND ITS USE

This application is a 371 of PCT/EP99/03110 filed May 6, 1999.

BACKGROUND OF THE INVENTION

The invention relates to an active ingredient-containing oral or mucosal preparation with controllable active ingredient release rate and its use.

Oral dosage forms ordinarily deliver their active ingredient by diffusion or disintegration, resulting in nonlinear release kinetics. A frequent requirement for oral pharmaceutical systems is that there be linear zero order active ingredient release from the administration form. It may additionally be desirable to be able to modulate as desired the release profile appropriate for specific requirements. Systems which achieve the desired effect are normally complicated and costly to produce.

Description of the Prior Art

The document U.S. Pat. No. 4,606,909 describes a pharmaceutical preparation for oral administration having a homogeneous core in an internal covering which is insoluble at pH below 7.5 but is soluble in the small bowel region, the material of the covering being selected from a group of acrylic polymers and each core consisting of a multiparticulate system of particles with an average size between 1 and 10 $\mu$m and the particles containing an active substance of low solubility.

WO 89/03437 describes a diffusion-controlled, multiparticulate oral formulation with active ingredient-containing individual units which are provided with a water-insoluble but water-diffusible covering comprising a combination of a water-dispersible film former and a polymeric substance to prevent adhesion of the units at elevated temperature, which imparts a certain flowability to the units. The covering has adequate plastic deformability which prevents a significant change in the release behaviour of the active ingredient from compressed or noncompressed units.

SUMMARY OF THE INVENTION

DE 39 18 801 A1 describes a product with controlled active ingredient delivery, which consists of multiparticulate articles having at least one active ingredient and at least one inactive component which controls the rate of active ingredient release and which comprises two to four layers. The invention in this case consists of the facts that a) the innermost layer consists of an inactive core or is identical to the outwardly following one, b) the outwardly following layer consists of active ingredient and possibly additionally of inactive component which is unsuitable in terms of nature or quantity for significantly controlling active ingredient release, c) the following layer contains the highest proportion of inactive component which controls the rate of release, and additionally solid ingredients of the nature of a matrix, and controls the rate, and d) possibly a further layer follows and controls rapid release of the active ingredient at the start but has a negligible effect on the rate of release.

The invention is based on the object of indicating an administration form for an active ingredient-containing oral or mucosal preparation which is less complicated and displays, using simple and cost-effective means, release kinetics which can be modulated as desired.

The object is achieved with an active ingredient-containing oral or mucosal preparation having a controllable active ingredient release rate of the type specified in the preamble of claim 1 by a configuration corresponding to the features indicated in claim 1.

The following definitions serve to explain the invention:

Preparation: A composition containing a first group of particles and at least one further group of particles which is not identical to the first group of particles.

Particles: By this are meant spherical and nonspherical particles with a size in the region above 10 $\mu$m. The upper limit of particle size is in principle not fixed, but for the intended purpose of use in the pharmaceutical or veterinary sector upper limits of 3 mm are preferred. The particles comprise a core and a covering which completely envelopes the core and which may also be referred to as coating layer. In a particular embodiment, the core of the particles may also be coated with more than one coating layer.

Core: The core is a spherical or nonspherical particle with a size in the region above 1 $\mu$m. The upper limit of the size of the core is in principle not fixed, but for the intended purpose of use in the pharmaceutical or veterinary sector an upper limit of 2 mm is preferred. Cores with sizes between 10 and 50 $\mu$m are preferred. The core contains a core substance and at least one active ingredient.

Coating layer: The coating layer covers the core of the particles completely. In the case of spherical cores, the coating layer has the shape of a hollow sphere. The coating layer or coating layers may likewise in principle be of any thickness. The thickness of the coating layer corresponds to the size of the particles minus the size of the core divided by 2. In the case of spherical particles with spherical cores, the thickness of the coating layer(s) corresponds to the radius of the particles minus the radius of the core. There is in principle no restriction on the thickness of the coating layer, that is to say there is in principle no upper limit. However, the thickness of the coating layer for a specific core is always essentially constant. For the intended pharmaceutical purposes, however, covering thicknesses between 10 and 1000 $\mu$m are preferred. Covering thicknesses between 10 and 100 $\mu$m are particularly preferred. The coating layer contains a coating substance and is essentially free of the active ingredient which is present in the core.

Group: A plurality of identical particles forms a group of particles. This means that all the particles in this group have the same uniform size of the core and the same uniform coating layer. Moreover, all the other properties of the particles which belong to a group of particles are essentially the same. The consequence of this is that a single group of particles accordingly shows in a particular medium a characteristic release behaviour for the active ingredient(s).

It is advantageous in the case of particles with identical core substance and identical covering substance, these necessarily being assigned to different groups according to the relative proportions by weight of core substance and covering substance, and identical groups displaying identical erosion and release behaviour, to make use of the possibility resulting therefrom for controlling the release kinetics of the active ingredient. This control is exerted via the mixing ratio of different groups of particles. For example, it is possible to select individual groups which differ from one another by a stepwise delay in the start of release. When groups of this type are combined in such a way that, for example, they start to release active ingredient sequentially at equal time intervals it is possible to control any desired course of active ingredient release or modulate as desired the time profile of release in accordance with specific requirements. This means that the composition according to the invention with controllable active ingredient release rate complies with the requirement that it is able to have release kinetics which can be modulated as desired using simple and cost-effective means. This is achieved without difficulty by any desired mixing ratio of the different groups of particles

DESCRIPTION OF THE PREFERRED EMBODIMENTS

Embodiments of the invention are provided in accordance with the dependent claims. Different particles may contain different active ingredients. However, it is also possible for different particles to contain active ingredients in different concentrations. A further possibility is for cores of different particles to differ in size or mass and/or composition of their active ingredient-containing substance. In addition to this, it may be particularly advantageous that the active ingredient-containing cores are soluble or insoluble, erodable or substantially non-erodable in the gastrointestinal tract.

Carrier substrate: By this is meant a substance which is able to take up a first group of particles and at least one other group of particles. It can be used in particular embodiments of the invention if, for example, the intention is to produce a composition which is homogeneous viewed macroscopically.

The invention also provides for the particles present in the carrier substrate to be a mixture of units of the same type. However, this does not rule out the possibility that the particles present in the carrier substrate are also a mixture of units of different types.

Carrier substrate is the designation given to a solid or flowable substance or mixture of substances which comprises the particle mixture. Substances of this type, which must be physiologically acceptable, are known in principle to the skilled worker. Depending on the requirement, rapidly melting substances are used in particular for the rectal or vaginal administration form. Examples suitable for use for this purpose are fats such as cocoa fat, hard fats (Witepsol®, Estarinum®, Novata®), macrogols and gelatins. The carrier substrate may additionally envelope a further stabilizing covering. This covering may be produced, for example, by hard or soft gelatin capsules. This covering, which must not be confused with coating layer covering the core of the particles, has the function merely of where appropriate taking up the preparation with or without carrier substrate. The invention does not rule out such a capsule, which is substantially dimensionally stable before administration, containing the particle mixture exclusively.

Release: Release is the name given to the delivery of the active ingredient(s) present in the core of the particles into the medium surrounding the particles. Controlled release is achieved according to the invention by using a first group of particles and at least one other group of particles which is not identical to the first group of particles. Since each of these nonidentical groups shows its own characteristic release behaviour for the active ingredient(s), simultaneous administration of these nonidentical groups results in the superimposition of nonidentical release behaviours.

Mixing ratio: The mixing ratio refers to the composition of the preparation and specifically to the composition in terms of quantity of the number of groups of particles present in the preparation. There are in principle no restrictions concerning possible mixing ratios. It is expedient (for example owing to the need to minimize production costs) for the number of groups of particles in the preparation to be kept as small as possible. However, the number of groups of particles may also be relatively large owing to specific therapeutic requirements (for example a plurality of active ingredients; very specific, for example, pulsatile, release). The preferred numbers of groups of particles are therefore 2, 3, 4 or 5. It is, of course, also possible for the preparation to contain up to 10 or more groups of particles, however. In the final analysis, the requirements of the particular use will determine the specific mixing ratio of the various groups of particles in the preparation. The invention relates to the use of a preparation containing a first group of particles and at least one other group of particles which is not identical to the first group of particles for achieving controlled release of an active ingredient present in the cores of the particles, in particular in the human and veterinary medical sectors.

The preparation is administered orally, rectally, vaginally etc. The release of active ingredient then takes place in the appropriate medium, and there is transmucosal absorption of the active ingredient.

One use of the preparation according to the invention provides for controllable release of active ingredient in the gastric fluid region. However, it is also possible to provide for controllable release of active ingredient in the gastrointestinal tract, especially in the small bowel. Such a difference arises in a manner known per se depending on the pH of the body fluid, on the one hand in the acidic region of the stomach, or on the other hand in the neutral or basic region of the small bowel. The preparation is preferably used for control, which can be modulated as desired, and in particular for linear control, of active ingredient release. Finally, the preparation can be used for the controllable release of active ingredient, for example in the form of an article such as a suppository in the anal or vaginal region.

Core substance: This substance has the function of being a carrier material for the active ingredient present in the core. It is possible to dispense with the use of a core substance if the properties of the active ingredient make the use of a carrier material superfluous or if the active ingredient or active ingredients are to be used in pure form.

The core substance of the individual particles usually contains besides one or more active ingredients and a carrier substance as filler also other auxiliaries as additions. The additions mentioned—also called auxiliaries—are divided according to their function into plasticizers, tackifiers, absorption promoters, stabilizers or flow regulators. Substances of these types, which must be physiologically acceptable, are known in principle to the skilled worker. The substances employed as carrier substance or fillers are those which have solubility, erosion or swelling properties appropriate for requirements. Examples of typical substances for this purpose are lactose, cellulose types, sugar alcohols such as, for example, mannitol and sorbitol, various starches and alginates.

Coating substance (covering substance): This comprises erodable material. This material is capable on contact with a medium of losing its structural integrity. The medium may be, for example, water, gastric fluid, acids, other liquids. However, it may also mean a chamber with parameters which are changed from normal conditions, such as, for example, a chamber with elevated temperature and/or elevated humidity (such as the human lung). Loss of structural integrity means that this substance loses its external and/or internal structure, for example through physical and/or chemical modification. By this are meant processes such as melting, dissolving, swelling and decomposing. Substances which are able to erode on contact with one of the said types of medium may be monomeric and/or polymeric substances and/or mixtures thereof.

Suitable monomeric coating substances include wax, salts such as NaCl, sugars such as sucrose and other substances. Suitable polymeric coating substances include substances which are soluble in gastric fluid or in the small bowel.

A further feature of the coating substance is the property of virtually no diffusion of active ingredient or active ingredients taking place through the coating substance. This means that the coating substance does not allow the active ingredients to pass through or that diffusion of the active ingredient(s) through the coating layer takes a longer time than the time between production of the particles and their use.

The core substance of a particle may, where appropriate, be identical to the coating substance of this particle; however, they may also be different materials. Where the core substance and coating substance are identical, the core may differ from the coating layer through the existence of the active ingredient or active ingredients.

Employed as coating substance soluble in gastric fluid are, for example, acrylic acid derivatives such as Eudragit®L and Eudragit®S, polyvinyl alcohols, hydroxypropylmethyl-cellulose acetate phthalate or cellulose acetate phthalate, and as substances soluble in the small bowel are polyacrylic esters such as, for example, Eudragit®E30D, polyacrylic acid derivatives, shellac or celluloses such as methyl- or ethylcellulose.

Active ingredients are substances which are able to exert a chemical or pharmaceutical effect. These include low and high molecular weight substances. Substances of these types are known to the skilled worker. The high molecular weight substances include, inter alia, enzymes, vaccines, insulin, peptides, proteins and biopolymers.

Suitable active ingredients belong to the active ingredient groups of parasympatholytics (for example scopolamine, atropine, berlactyzine), cholinergics (for example physostigmine, nicotine), neuroleptics (for example chlorpromazine, haloperidol), monoamine oxidase inhibitors (for example tranylcypromine, selegiline), sympathomimetics (for example ephredine, D-norpseudoephedrine, salbutamol, fenfluramine), sympatholytics and antisympathotonics (for example propranolol, timolol, bupranolol, clonidine, dihydroergotamine, naphazoline), anxiolytics (for example diazepam, triazolam), local anaesthetics (lidocaine), central analgesics (for example fentanyl, sufentanil), antirheumatics (for example indomethacin, piroxicam, lornoxicam), coronary therapeutic agents (for example glycerol trinitrate, isosorbide dinitrate), oestrogens, gestagens and androgens, antihistamines (for example diphenhydramine, clemastine, terfenadine), prostaglandin derivatives, vitamins (for example vitamin E, cholecalciferol) and cytostatics.

BRIEF DESCRIPTION OF THE DRAWINGS

Further details, features and advantages of the invention are evident from the following explanation of an exemplary embodiment depicted diagrammatically in the drawings. These show:

The oral or mucosal preparation with a controllable active ingredient release rate depicted in FIG. 1 has a carrier substrate 1 with incorporated particles 2 consisting of a core 3 and of an active ingredient-free covering 4. The active ingredient-free covering can, according to the invention be eroded in the moist or aqueous medium of a body fluid. This may be any type of fluid such as, for example, gastric or intestinal fluid, fluids in the oral cavity or else other body cavities, for example in the anal or vaginal region. It is additionally essential that the carrier substrate 1 is a preparation which rapidly disintegrates in the moist or aqueous medium of a body fluid and releases the particles 2. In this case it is possible for particles 2 with identical core substance and identical covering substance to be assigned to different groups depending on their relative proportions by weight, with identical groups displaying identical erosion and release behaviour. The means for controlling the release kinetics of the active ingredient is then the mixing ratio of different groups of particles 2. FIGS. 1 to 5 show in this connection various embodiments of the invention. As FIG. 1 shows concerning this, cores 3 of different particles 2 may contain identical active ingredient (A), it being possible for this active ingredient to be present in different concentrations. In FIG. 2, cores 2 of different particles 3 contain different active ingredients (A, B, C). FIG. 3 shows an embodiment of the invention in which a plurality of active ingredients (A–D) are present in cores 2 of particles 3, it being possible for the active ingredient mixture to be different in different cores 2. As FIG. 4 shows, it is additionally possible for cores 3 of different particles 2 to differ in size or mass and/or composition of their active ingredient-containing substance. It is further possible for the thickness and/or material nature or composition of the covering 4 of individual particles 2 to be different (FIG. 5).

Figure 1:
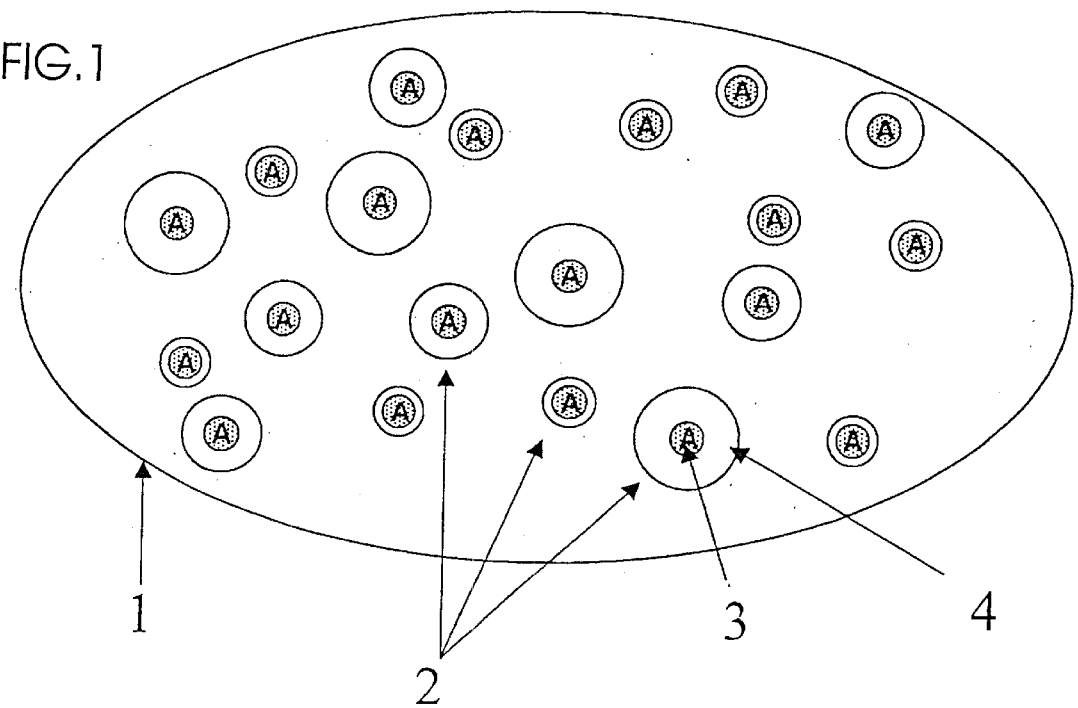
FIG. 1: a carrier substrate 1 with incorporated diverse particles 2 with identical core substance 3, identical active ingredient A, identical coating substance and different coating thickness 4.
Figure 2:
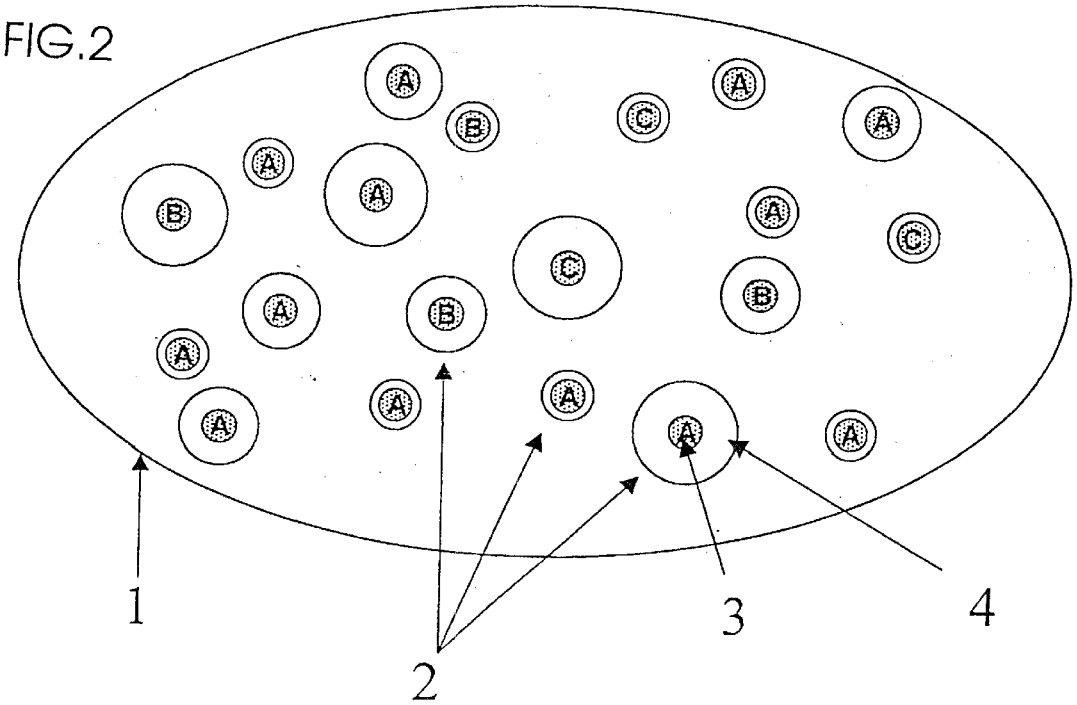
FIG. 2: a carrier substrate 1 with incorporated diverse particles 2 with identical core substance 3, different active ingredients A–C, identical coating substance and different coating thickness 4.
Figure 3:
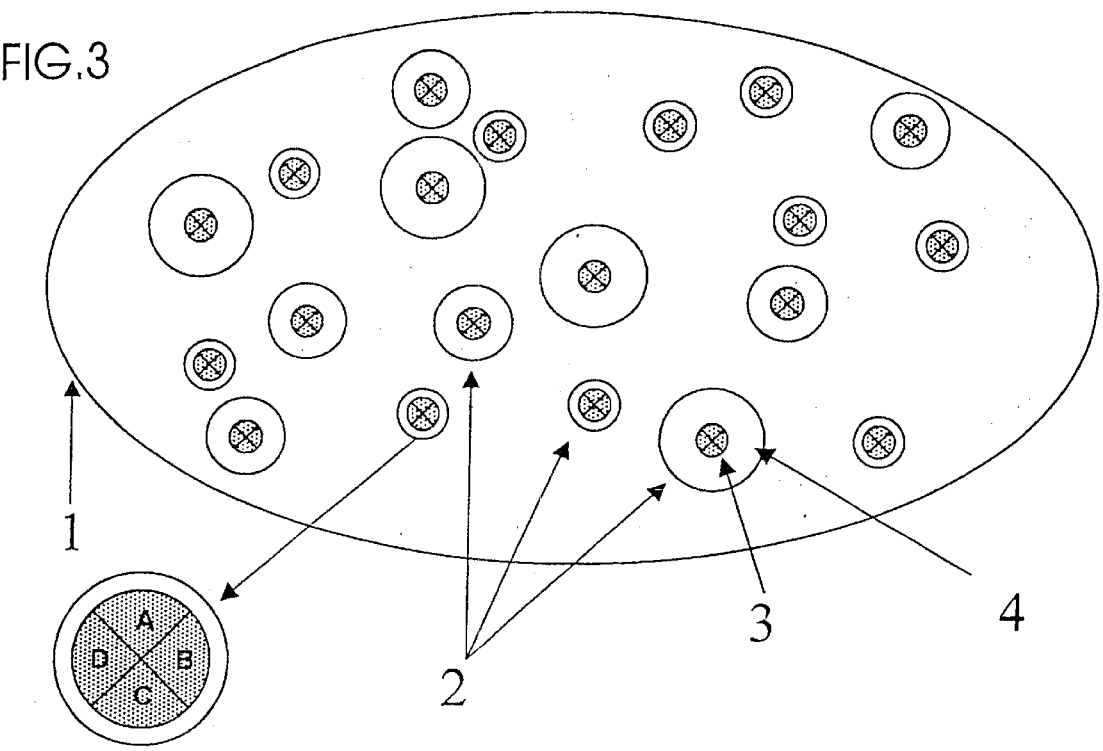
FIG. 3: a carrier substrate 1 with incorporated diverse particles 2 with identical core substance 3, a plurality of active ingredients A–D in each particle core, identical coating substance and different coating thickness 4.
Figure 4:
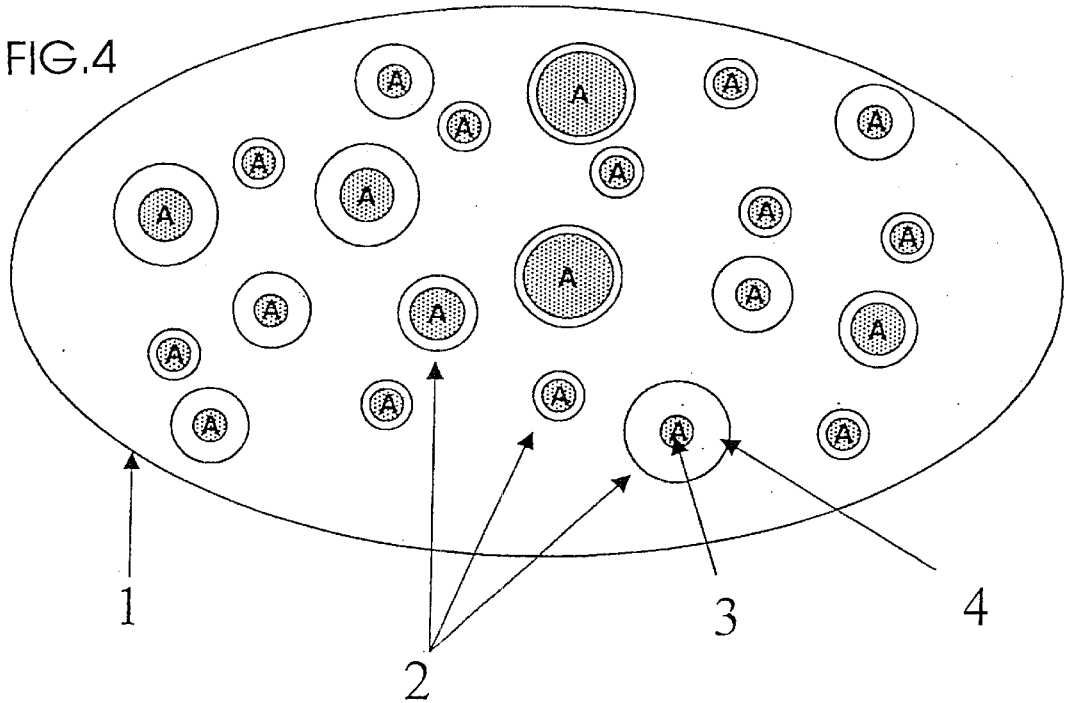
FIG. 4: a carrier substrate 1 with incorporated diverse particles 2 with different core substance 3 and different core radius, identical active ingredient A, identical coating substance and different coating thickness 4.
Figure 5:
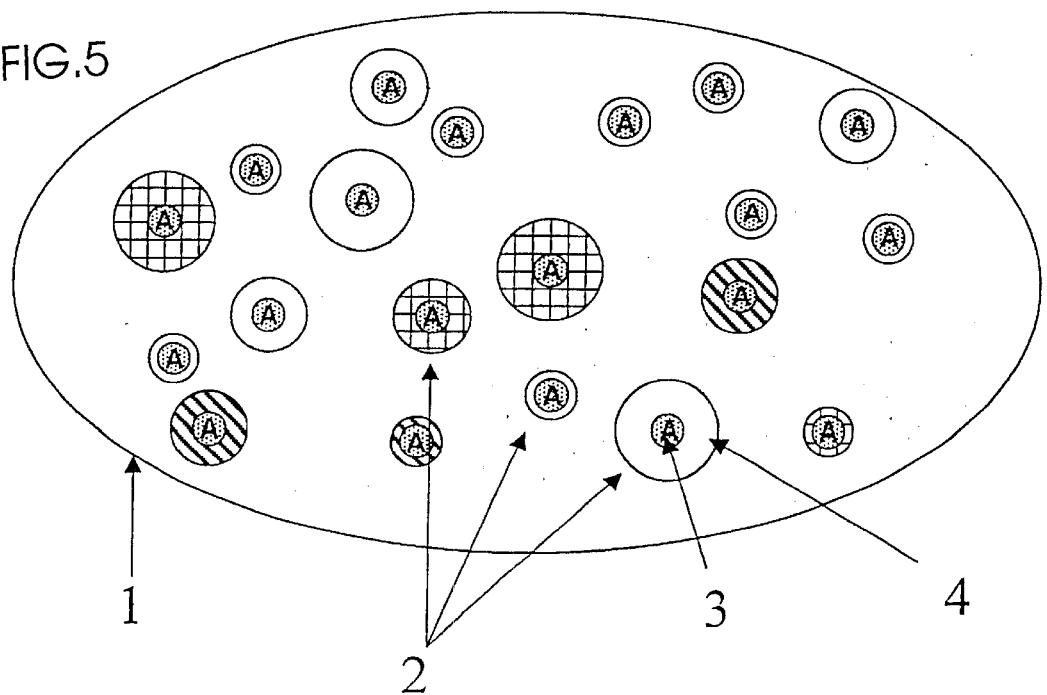
FIG. 5: a carrier substrate 1 with incorporated diverse particles 2 with identical core substance 3, identical active ingredient A, different coating substance and coating thickness 4.

As FIG. 1 also shows, the particles 2 present in the carrier substrate 1 may be a mixture of units of identical type or different types.

Figure 6:
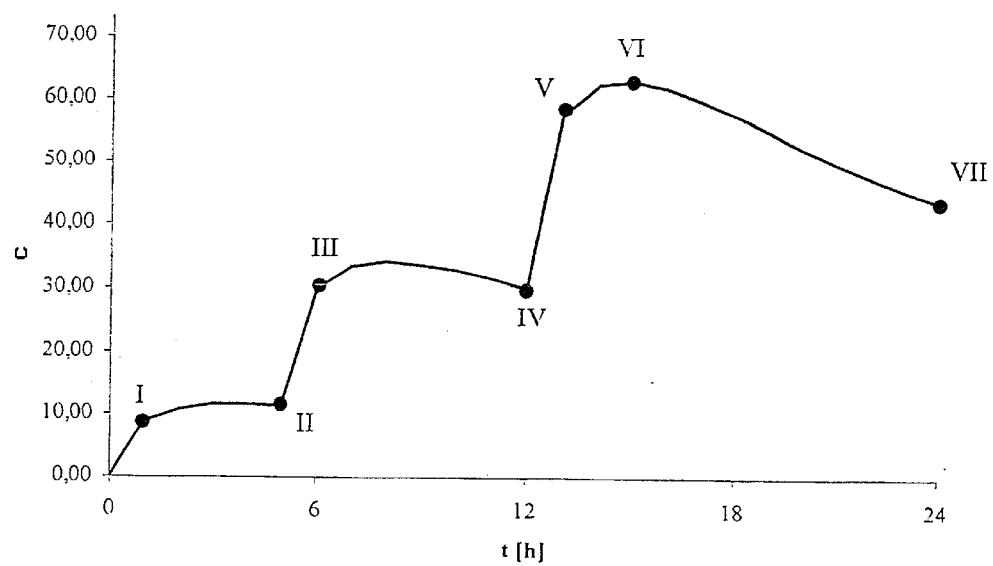
FIG. 6: a diagram of a release profile of active ingredient as a function of time.

FIG. 6 shows a release profile of active ingredient during an active ingredient release extending over a prolonged period. For this purpose, the time between 0 and 24 h is indicated on the abscissa, and the amount of active ingredient delivered is indicated on a scale between 0 and 70 (for example $\mu$g) on the ordinate. The course of the diagram between 0 and I shows a comparatively steep but linear increase in the delivery of active ingredient after exposure of an active ingredient-containing core 3 as a result of preceding erosion of an active ingredient-free covering 4. The subsequent course of the plot in the diagram between I and II ensures exhaustion of the active ingredient content from a first group of particles, after which the coverings of a second group are eroded, approximately after 5½ h, and between points II and III on the plot there is again a pronounced linear increase in the plot until, after between 6 and 12 h, corresponding to branches III and IV of the plot, the active ingredient content in the exposed cores 3 is consumed and the active ingredient content in the body slowly declines again until, at the start of the twelfth hour, another group of particles continues, after erosion of the core coverings, the delivery of active ingredient in the steep course of the plot from IV to V, with the maximum active ingredient concentration in the body, about 65 μg, being reached at point VI. After exhaustion of the active ingredient content in the last group, the active ingredient content in the body then declines during the next approximately 8 h between points VI and VII from about 65 μg to about 40 μg.

The preparation according to the invention can be produced by processes which may represent combinations of the following steps which are known individually to the skilled worker:
1) production of the active ingredient-containing cores of the first group of particles,
2) production of the active ingredient-containing cores of a second group of particles,
3) coating of the active ingredient-containing cores of the first group of particles with a first coating layer,
4) coating of the active ingredient-containing cores of the second group of particles with a second coating layer, where either the cores of the first group of particles are not identical to the cores of the second group of particles, or the first coating layer is not identical to the second coating layer,
5) mixing the first group of particles and the second group of particles.

The chronological sequence of these steps is limited to the extent that the mixing (step 5) can take place only after production of the two groups of particles.

The active ingredient-containing cores can be produced in a single step if the first group of particles differs from the second group of particles only by different coating layers. It is likewise possible to produce the coating layers in a single step as long as the first group of particles differs from the second group of particles only by different active ingredient-containing cores.

The cores can be produced, for example, in a ball mill, and the coating layer can be produced, for example, in a spray-coater. The process described in DE 197 11 393 C1 can be used for coating cores with a size below 100 μm with coating layers with a layer thickness between <1 μm and up to a few μm, for example.

The invention is uncomplicated and makes it possible with simple means to control the release kinetics of the active ingredient as desired and as a function of the mixing ratio of different groups of particles, and thus achieves the object stated at the outset in an optimal manner.

The invention has been described with particular emphasis on the preferred embodiments, but variations and modifications within the spirit and scope of the invention may occur to those skilled in the art to which the invention pertains.

What is claimed is:

1. An active ingredient-containing oral or mucosal preparation with controllable active ingredient release, which contains a plurality of particles to form a multiparticulate system, each particle consisting of an active ingredient-containing core and of a covering which is substantially free of active ingredient and is erodable or soluble in the moist or aqueous medium of a body fluid, and the multiparticulate system containing the particles on or in a carrier substrate, and the carrier substrate being a preparation which rapidly disintegrates in the moist or aqueous medium of a body fluid and releases the particles, characterized
   in that particles with identical core substance and identical covering substance are to be assigned to different groups according to their relative proportions by weight, with identical groups displaying identical erosion and release behaviour, and
   in that cores of different particles contain active ingredient in different concentrations, and
   in that the means for controlling the release kinetics of the active ingredient is the mixing ratio of different groups of particles.

2. A preparation according to claim 1, characterized in that cores of different particles contain different active ingredients.

3. A preparation according to claim 1 or 2, characterized in that cores contain a plurality of active ingredients.

4. A preparation according to claim 1, wherein cores of different particles differ in size or mass and/or composition of their active ingredient-containing substance.

5. A preparation according to claim 1, wherein the particles present in the carrier substrate are a mixture of units of identical type.

6. A preparation according to claim 1, wherein the particles present in the carrier substrate are a mixture of units of different types.

7. A preparation according to claim 1, wherein cores of different particles are substantially insoluble in the acidic and/or basic region of the gastrointestinal tract.

8. A preparation according to claim 1, wherein cores of different particles are soluble in the acidic and/or basic and/or neutral region of the gastrointestinal tract, with the solubility of the cores differeing from the solubility of their covering by at least 10%.

9. A preparation comprising a first group of mutually identical particles and at least one other group of mutually identical particles, characterized in that
   a) the particles of the first group have a core and a coating layer,
   b) the particles of the at least one other group have a core and a coating layer,
   c) the mutually identical particles of the first group are not identical to the mutually identical particles of the at least one other group,
   d) the core of the particles of the first group has a particular weight GK1,
   e) the coating layer of the particles of the first group has a particular weight GU1,
   f) said weights of core and coating layer of the particles of the first group are in a particular constant ratio GK1:GU1,
   g) the core of the particles of the at least one other group has a particular weight GKn,
   h) the coating layer of the particles of the at least one other group has a particular weight GUn,
   i) the said weights of core and coating layer of the particles of the at least one other group are in a particular constant ratio GKn:GUn, and the ratio GK1:GU1 is not identical to the ratio GKn:GUn.

10. A preparation according to claim 9, wherein
   a) the active ingredient present in the core of the particles of the first group and the active ingredient present in the core of the particles of the at least one other group are identical, and b) the coating layer of the particles of the first group and the coating layer of the at least one other group are not identical.

11. A preparation according to claim 9, wherein the active ingredient present in the core of the particles of the first group and the active ingredient present in the core of the particles of the at least one other group are not identical.

12. A process for the production of a preparation comprising a first group of mutually identical particles and at least one other group of mutually identical particles, where the mutually identical particles of the first group are not identical to the mutually identical particles of the at least one other group, characterized by steps:
   a) production of the active ingredient-containing cores of the first group of particles,
   b) production of the active ingredient-containing cores of a second group of particles,
   c) coating of the active ingredient-containing cores of the first group of particles with a first coating layer,
   d) coating of the active ingredient-containing cores of the second group of particles with a second coating layer, where either the cores of the first group of particles are not identical to the cores of the second group of particles, or the first coating layer is not identical to the second coating layer, and
   e) mixing the first group of particles and the second group of particles.

13. A method for the controllable release of active ingredients in the gastric fluid region having a body fluid having a moist or aqueous medium, comprising the steps of:
   applying an active ingredient-controlling preparation with controllable active ingredient release in the gastric fluid region, said preparation comprising a plurality of particles to form a multiparticulate system, each particle consisting of an active ingredient-containing core and a covering which is substantially free of active ingredient (s) and is erodable or soluble in the moist or aqueous medium of the body fluid of said region, and the multiparticulate system containing the particles on or in a carrier substrate, the carrier substrate being a preparation which rapidly disintegrates in the moist or aqueous medium of the body fluid and releases the particles;
   rapidly disintegrating said preparation in the moist or aqueous medium of a body fluid of said region to release said plurality of particles in said medium; and
   assigning particles with identical core substance and identical covering substance to different groups according to their relative proportions by weight, with identical groups displaying identical erosion and release behavior;
   wherein cores of different particles contain active ingredient(s) in different concentrations and wherein the means for controlling the release kinetics of the active ingredient(s) is the mixing ratio of different groups of particles.

14. The method according to claim 13 wherein said preparation is applied in the gastrointestinal tract.

15. The method according to claim 14 wherein said gastrointestinal tract is the small bowel.

16. The method according to claim 13 wherein said preparation is modulated to achieve the linear control of active ingredient release.

17. The method according to claim 13 wherein said preparation is a suppository for use in the anal or vaginal region.

* * * * *

UNITED STATES PATENT AND TRADEMARK OFFICE
CERTIFICATE OF CORRECTION

PATENT NO. : 6,635,276 B1
DATED : October 21, 2003
INVENTOR(S) : Christian Von Falkenhausen It is certified that error appears in the above-identified patent and that said Letters Patent is hereby corrected as shown below:

<u>Title page,</u>
Item [73], Assignee, correct the spelling of assignee's name from "KTS Kignabb Therapie-Systeme AG" to -- LTS Lohmann Therapie-Systeme AG --.

Signed and Sealed this

Sixteenth Day of March, 2004

JON W. DUDAS
*Acting Director of the United States Patent and Trademark Office*